United States Patent [19]

Matuo et al.

[11] 3,936,449

[45] Feb. 3, 1976

[54] ANTI-ARRHYTHMIC AGENTS

[75] Inventors: Ichiro Matuo, Machida; Sadao Ohki, Tokyo, both of Japan

[73] Assignee: Sadao Ohki, Tokyo, Japan

[22] Filed: Apr. 11, 1974

[21] Appl. No.: 459,971

[52] U.S. Cl..... ............. 260/247.2 A; 260/268 TR; 260/293.61; 260/295 T; 260/326 C; 260/343.3 R; 424/248; 424/267; 424/274

[51] Int. Cl.² ............... C07D 295/02; C07D 295/00

[58] Field of Search...260/247.2 A, 268 TR, 293.61, 260/326 C

[56] References Cited
UNITED STATES PATENTS

| | | | |
|---|---|---|---|
| 3,607,876 | 9/1971 | Bailey........................... | 260/294 AC |
| 3,850,921 | 11/1974 | Matuo et al. ................ | 260/247.2 A |
| 3,850,922 | 11/1974 | Matuo et al. ................ | 260/247.2 A |

*Primary Examiner*—Lorraine A. Weinberger
*Assistant Examiner*—P. J. Killos
*Attorney, Agent, or Firm*—Robert E. Havranek

[57] ABSTRACT

A series of 5-endo-carbamoyloxy-N-[amino(lower)-alkyl]bicyclo[2.2.1]heptane-2,3-di-endo-carboxylic acid imides have been found to possess unique prophylactic and therapeutic activity as anti-arrhythmia agents. An example of such a compound possessing excellent activity is 5-endo-phenylcarbamoyloxy-N-(3-dimethylaminopropyl)bicyclo[2.2.1]heptane-2,3-diendo-carboxylic acid imide hydrochloride.

16 Claims, No Drawings

ANTI-ARRHYTHMIC AGENTS

BACKGROUND OF THE INVENTION

1. Field of the Invention

This invention relates to a novel series of 5-endo-substituted-carbamoyloxy-N-[amino(lower)alkyl]bicyclo[2.2.1]heptane-2,3-di-endo-carboxylic acid imides possessing anti-arrhythmic and/or anti-fibrillatory activity.

2. Description of the Prior Art

A. British Patent No. 1,042,840 describes compounds having the formula

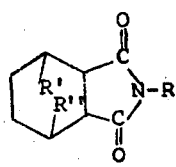

in which each of R' and R'' represent hydrogen, or together an alkylene group having 1 or 2 carbon atoms, and R represents an alkyl group having 6 to 18, preferably 8 to 12 carbon atoms in a straight chain as having particularly advantageous properties as functional fluids.

B. U.S. Pat. No. 2,393,999 describes the compound having the formula

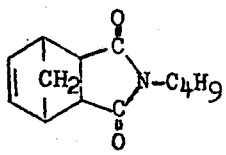

as being an effective insecticide.

C. U.S. Pat. No. 2,424,220 describes the compound having the formula

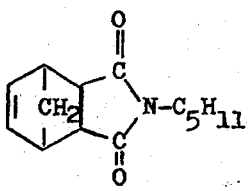

as being an effective insecticide.

D. U.S. Pat. No. 2,462,835 describes the compound having the formula

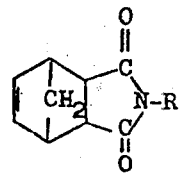

in which R is alkyl, alkene, aryl, substituted aryl, alkynyl, etc. as insecticides.

E. Culberson and Wilder, Jr., J. Org. Chem., 25, pp. 1358–62 (1960) report the preparation of compounds having the formula ,30/16

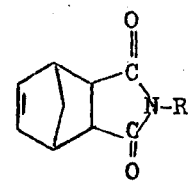 and 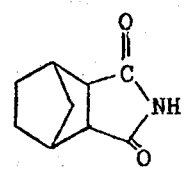

in which R is $CH_3$, $C_6H_{13}$ or hydrogen.

F. Rice, Reide and Grogan, J. Org. Chem., 19 pp. 884–893 (1954) report the preparation of compounds of the formula

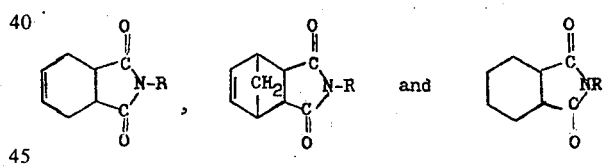

in which R is alkyl and their subsequent reduction with lithium aluminum hydride.

B. Worall, J. Am. Chem. Soc., 82, pp. 5707–5711 (1960) report the preparation of compounds having the formula

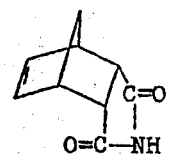 , 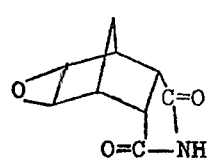 ,

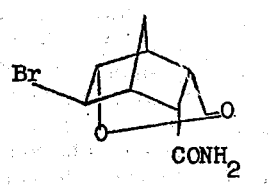 and 

C. German Auslegeschrift No. 1,179,205 reports the preparation of compounds having the formula

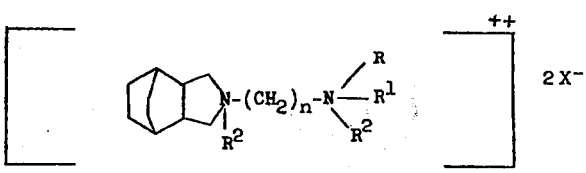

in which the bicyclo [2.2.2]octane ring system is saturated or unsaturated and/or substituted, R and $R^1$ are alkyl and alkenyl groups of 1 to 5 carbon atoms, or when combined with the nitrogen a heterocyclic ring. $R^2$ is a (lower) alkyl group, n is a number of 2 to 5 and X a halogen anion. The quaternary compounds are described as having therapeutic properties in the treatment of cardiovascular disease, specifically high blood pressure.

SUMMARY OF THE INVENTION

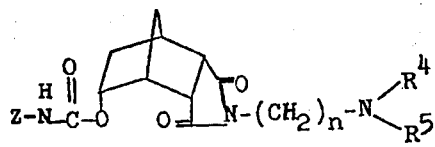

in which Z is 3 or 4-pyridyl, (lower)alkyl, cyclohexyl, cyclopentyl, cycloheptyl, 1-adamantyl, cyclobutyl, cyclopropyl or a radical of the formula

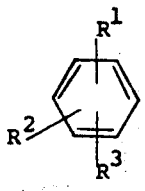

wherein $R^1$, $R^2$ and $R^3$ are alike or different and each is H, Cl, Br, F, (lower)alkyl, nitro, OH or (lower)alkoxy, n is an integer of 2 to 4 inclusive and $R^4$ or $R^5$ is H, (lower)alkyl or when taken together with the nitrogen a radical of the formula

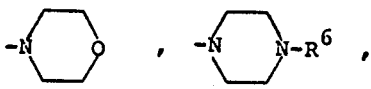

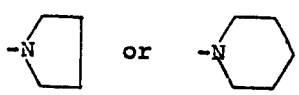

in which $R^6$ is (lower)alkyl; or a pharmaceutically acceptable acid addition salt thereof are antiarrhythmic agents.

Cardiac arrhythmia, a phenomenon commonly associated with coronary heart disease or myocardial infarction, is an affliction not uncommon in humans, especially the elderly. The mechanism of cardiac arrhythmia is suspected to be caused by an abnormal "focus" in the ventricle of the heart which sends out (fires) nerve signals more rapidly than required for the normal beating of the heart. Uncontrolled arrhythmia can lead to fibrillation which results in death.

It has been discovered that the series of compounds herein designated 5-endo-substituted-carbamoyloxy-N-[amino-(lower)alkyl]bicyclo[2.2.1]heptane-2,3-di-endo-carboxylic acid imides having the formula

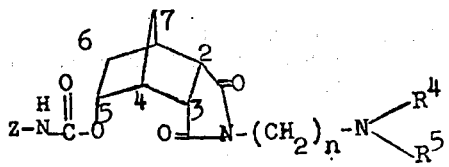

in which Z is (lower)alkyl, cyclohexyl, cyclopentyl, cyclobutyl, cycloheptyl, cyclopropyl or a radical of the formula

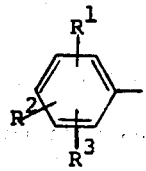

wherein $R^1$, $R^2$ or $R^3$ is H, Cl, Br, F, (lower)alkyl, nitro, OH or (lower)alkoxy, n is an integer of 2 to 4 inclusive and $R^4$ or $R^5$ is H, (lower)alkyl or when taken together with the nitrogen a radical of the formula

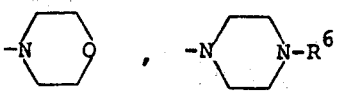

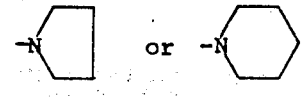

in which $R^6$ is (lower)alkyl; or a pharmaceutically acceptable acid addition salt thereof are useful therapeutic or prophylactic agents in the suppression of the abnormal ectopic beat.

Compound I can theoretically exist in several isomeric forms, namely;

A. endo-carbamoyloxy:endo-substituted imide;
B. exo-carbamoyloxy:exo-substituted imide (X); C. endo-carbamoyloxy:exo-substituted imide; and
D. exo-carbamoyloxy:endo-substituted imide.

Furthermore, each of these isomers has two optical isomers; levorotatory and dextrorotatory.

The distinction between the isomers is determined by the relative position of the constituent bonds at positions 2, 3 and 5 of the bicyclo ring system.

When these bonds, i.e., the constituent bonds at positions 2, 3 and 5, are on the same side as the $C_7$ bridge, we have the exo-exo isomer. When these bonds, i.e., the constituent bonds at positions 2, 3 and 5 are on the opposite side of the $C_7$ bridge or alternately within the cage formed by carbon atoms 2,3,5 and 6, then we have the endo-endo isomer. When the constituent bond at position 5 is on the same side as the $C_7$ bridge and the constituents bond 2 and 3 are on the opposite side of the $C_7$ bridge, then we have the exo(5-position)-endo(2,3-position) isomer. Illustrative of the exo-exo isomer is the compound having the formula

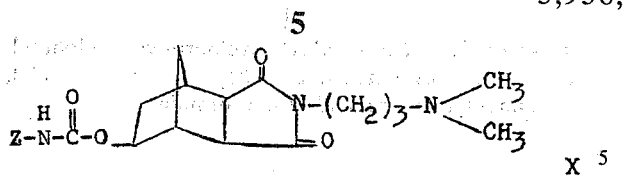

Illustrative of endo-endo is the compound of formula I.

The only isomers claimed in this invention are the endo-endo isomers as represented by compound I and the dextro- and levorotatory isomers thereof. The endo-endo isomers are inherently exclusively produced by the synthesis described herein.

The optical isomers can be separated and isolated by fractional crystallization of the diastereoisomeric salts formed, for instance, with (+) or (−)-tartaric acid or D-(−) camphor sulfonic acid (see experimental).

For the purpose of this disclosure, the term "(lower)alkyl" is defined as an alkyl radical containing 1 to 6 carbon atoms. The term "(lower)alkoxy" is an alkoxy radical containing 1 to 6 carbon atoms. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula I with hydrochloric, sulfuric, nitric, phosphoric, phosphruous, hydrobromic, maleic, malic, ascorbic, citric or tartaric, pamoic, lauric, stearic, palmitic, oleic, myristic, laurylsulfonic, napthalenesulfonic, linoleic or linolenic acid, and the like.

A preferred embodiment of the present invention is the compound having the formula

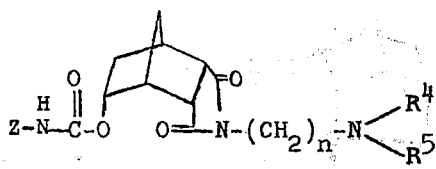

in which Z is 3 or 4-pyridyl, 1-adamantyl, (lower)alkyl, cyclohexyl, cyclopentyl, cyclobutyl, cycloheptyl, cyclopropyl, or a radical of the formula

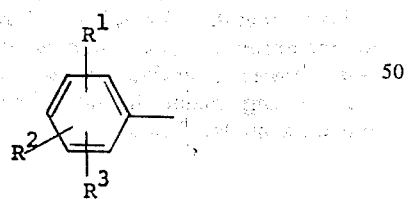

wherein $R^1$, $R^2$ or $R^3$ is H, Cl, Br, F, (lower)alkyl, nitro, OH or (lower)alkoxy, n is an integer of 2 to 4 inclusive and $R^4$ or $R^5$ is H, (lower)alkyl or when taken together with the nitrogen a radical of the formula

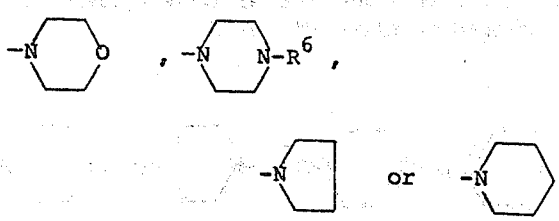

in which $R^6$ is (lower)alkyl; or a pharmaceutically acceptable acid addition salt thereof.

Another preferred embodiment of the present invention is the compound having the formula

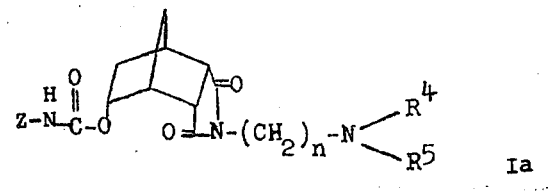

in which Z is a radical of the formula

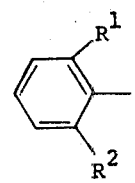

wherein $R^1$ and $R^2$ are alike or different and each is H, Cl, Br, F, (lower)alkyl, nitro, OH or (lower)-alkoxy, n is an integer of 2 to 4 inclusive and $R^4$ and $R^5$ is H, (lower)alkyl or when taken together with the nitrogen a radical of the formula

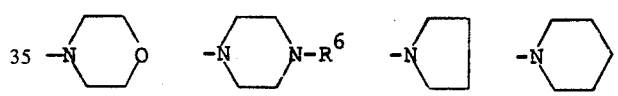

in which $R^6$ is (lower)alkyl; or a pharmaceutically acceptable acid addition salt thereof.

Another preferred embodiment is the compound of formula Ia wherein $R^1$ and $R^2$ are alike or different and each is H, F, Cl, nitro or (lower) alkyl, $R^4$ and $R^5$ are H, (lower)alkyl or when taken together with the nitrogen a radical of the formula

Another preferred embodiment is the compound of formula Ia wherein $R^1$ and $R^2$ are (lower)alkyl, $R^4$ and $R^5$ are (lower)alkyl or when taken together with the nitrogen a radical of the formula

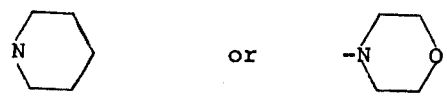

A more preferred embodiment is the compound of formula Ia wherein $R^1$ is hydrogen, $R^2$ is methyl, n is an integer of 3 and $R^4$ and $R^5$ are methyl; or the hydrochloride salt thereof.

A most preferred embodiment of the present invention is the compound of formula Ia wherein $R^1$ and $R^2$ are hydrogen, n is an integer of 3 and $R^4$ and $R^5$ are methyl; or the hydrochloride salt thereof.

A more preferred embodiment is the compound of formula I*a* wherein R¹ and R² are hydrogen, *n* is and integer of 2 and R⁴ and R⁵ are methyl; or the hydrochloride salt thereof.

A more preferred embodiment is the compound of formula I wherein R¹ and R³ are hydrogen, R² is p-nitro, *n* is an integer of 3 and R⁴ and R⁵ taken together with the nitrogen is a radical of the formula

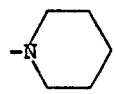

or the hydrochloride salt thereof.

A more preferred embodiment is the compound of formula I wherein R¹ and R³ are hydrogen, R² is p-chloro, *n* is an integer of 3 and R⁴ and R⁵ taken together with the nitrogen is a radical of the formula

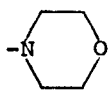

of the hydrochloride salt thereof.

A more preferred embodiment is the compound of formula I wherein R¹ and R³ are hydrogen, R² is p-nitro, *n* is an integer of 3 and R⁴ and R⁵ when taken together with the nitrogen is a radical of the formula

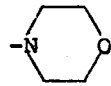

of the hydrochloride salt thereof.

A more preferred embodiment is the compound of formula I wherein R¹ and R³ are hydrogen, R² is p-chloro, hydrogen or p-nitro, *n* is an integer of 3 and R⁴ and R⁵ are each (lower)alkyl; or the hydrochloride salt thereof.

A more preferred embodiment is the compound of formula I wherein R¹ and R³ are hydrogen, R² is p-methyl, *n* is an integer of 3 and R⁴ and R⁵ are methyl; or the hydrochloride salt thereof.

A most preferred embodiment is the levorotatory isomers of the compound of formula I*a*.

Another most preferred embodiment is the dextrorotatory isomers of the compound I*a*.

The most preferred embodiment of the present invention is the dextrorotatory isomer of the compound I wherein R¹, R² and R³ are hydrogen, *n* is 3 and R⁴ and R⁵ are methyl; or the hydrochloride salt thereof.

Another most preferred embodiment of the present invention is the levorotatory isomer of the compound I wherein R¹, R² and R³ are hydrogen, *n* is 3 and R⁴ and R⁵ are methyl; or the hydrochloride salt thereof.

The objectives of the present invention have been achieved by the process of preparing the compounds having the formula

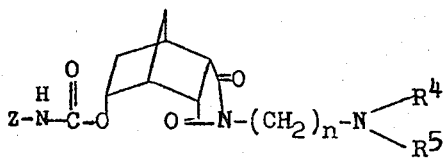

in which Z is (lower)alkyl, cyclopropyl, cyclobutyl, cyclopentyl, cyclohexyl, cycloheptyl, 3 or 4-pyridyl, 1-adamantyl or a radical of the formula

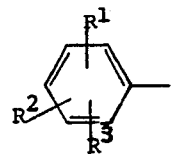

wherein R¹, R² or R³ is H, Cl, Br, F, (lower)alkyl, nitro, OH or (lower)alkoxy, *n* is an integer of 2 to 4 inclusive and R⁴ or R⁵ is H, (lower)alkyl or when taken together with the nitrogen a radical of the formula

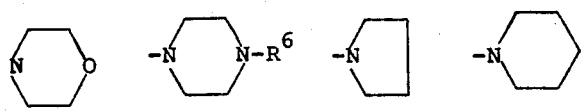

in which R⁶ is (lower)alkyl; which process comprises the consecutive steps of

A. treating a suspension of endo-cis-bicyclo[2.2.1-]hept-5-ene-2,3-dicarboxylic anhydride or exo-cis-bicyclo[2.2.1]hept-5-ene-2,3-dicarboxylic anhydride in water, but preferably the endo-cis isomer, with excess concentrated sulfuric acid at a temperature in the range of 70°–95° C. to produce the endo-endo compound having the formula

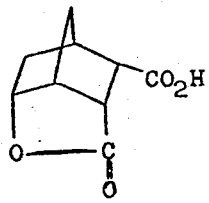

B. treating 1 mole of compound II with at least one mole of acetyl chloride or phosphorous trichloride at reflux temperature for at least 15 minutes and removing the excess acetyl chloride or phosphorous trichloride in vacuo to produce an oily residue II*a*;

C. treating residue II*a* with at least one mole of an amine having the formula

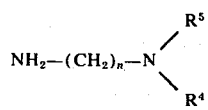

in which *n* is an integer of 2 to 4 inclusive, R⁴ or R⁵ are H, (lower)alkyl or when both are taken together with the nitrogen a radical of the formula

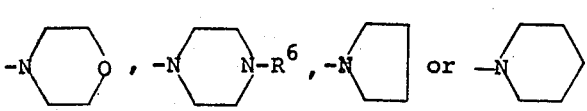

in which $R^6$ is (lower)alkyl; in an organic solvent, preferably selected from the group comprising benzene, toluene, xylene, and the like at about reflux temperatures for at least 30 minutes and removing the solvent in vacuo to produce an oily residue IIb;

D. treating residue IIb with at least one mole of potassium hydroxide in a mixture of a (lower)alkanol and water with the aid of heat, but preferably at reflux temperature for at least one hour to produce the compound having the formula

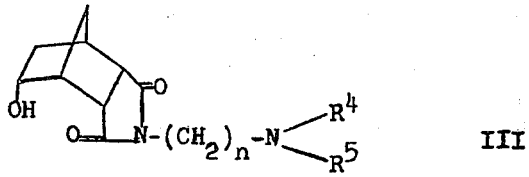 III in which $n$, $R^4$ and $R^5$ are as above; and

E. treating one mole of compound III with at least one mole of an isocyanate having the formula
Z-NCO
in which Z is (lower)alkyl, cyclopropyl, cyclobutyl, cyclopentyl, cyclohexyl, cycloheptyl, 3- or 4-pyridyl, 1-adamantyl or a radical of the formula

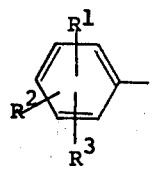

in which $R^1$, $R^2$ and $R^3$ are as defined above, in an organic solvent, preferably selected from the group comprising benzene, toluene, xylene, pryidine, but preferably pyridine, in a temperature range of 0° C. to 60° C., but preferably at about room temperature to yield compound I.

The compounds were tested in dogs for their reversion activity in ouabain-induced arrhythmia.

Anesthetized dogs were used for the production of ouabain-induced ventricular arrhythmias. The arrhythmia consisted of a nodal or ventricular tachycardia. The procedure used to establish the arrhythmia as well as the criteria employed to determine anti-arrhythmic activity generally was that employed by Lucchesi et al. Intravenous infusion of 1, 2 and 3 was done at a rate of 0.2 mg./kg./min. and compared to lidocaine and quinidine. The average reverting doses are shown below.

| Compound | I.V. Reverting Dose, mg./kg.* |
|---|---|
| 1 | 2.0 ± 0.58 (N=4) |
| 2 | 1.3 ± 0.28 (N=7) |
| 3 | 3.0 (N=3) |
| Quinidine | 4.9 |
| Lidocaine | 6.6 |

*Values are mean ± Standard Error; N = No. of Experiments.

The compounds were also tested for their reversion of ventricular arrhythmia due to coronary artery ligation in conscious dogs:

Multifocal ventricular ectopic rhythms were produced in dogs according to the coronary artery ligation method of Harris[2]. Approximately 24 hours after induction of the ventricular arrhythmia the test drugs were infused at a rate of 0.2 mg./kg./min. The approximate average doses necessary to produce a 50% decrease in the number of ventricular ectopic beats, and to produce reversion of the ventricular arrhythmia are shown below. In contrast to 1,2 and 3, no reversion was observed with an intravenous infusion of lidocaine or quinidine in doses of up to 20 mg./kg.

| Compound | I.V. Dose Producing 50% Reduction in Ectopic Beats (mg./kg.) | I.V. Reverting Dose (mg./kg.) |
|---|---|---|
| 1 | 2* (N=4) | 15 (N=4) |
| 2 | 1.5 (N=4) | 10 (N=4) |
| 3 | 2 (N=3) | 15 (N=3) |
| Lidocaine | >20 | >20 |
| Quinidine | 10.1 | >20 |

*Values are means, N = No. of experiments.

| Local Anesthetic Activity in Guinea Pigs | |
|---|---|
| Compound | ED$^{50}$ in mmoles of drug |
| 1 | 24 |
| 2 | 25 |
| 3 | 82 |
| Lidocaine | 23 |

References

1. Lucchesi, B. L. and H. F. Hardman: The influence of dichloroisoproterenol (DCI) and related compounds upon ouabain and acetylstrophanthidin induced cardiac arrhythmias. J. Pharmacol. Exp. Therap., 132:372, 1961.

2. Harris, A. S.: Delayed development of ventricular ectopic rhythms following experimental coronary occlusion. Circulation 1:1318, 1950.

All the compounds within the scope of the present invention possess anti-arrhythmic activity.

The compounds of the present invention are useful in the treatment of cardiac arrhythmia in mammals, including man, as prophylactic or therapeutic agents in doses in the range of 0.25 mg. to 3.0 mg./kg. up to 3 or 4 times a day.

EXPERIMENTAL

EXAMPLE 1

Preparation of Bicyclo[2.2.1]heptane-endo-2,3-dicarboxylic acid-5-endo-hydroxy-γ-lactone (II).

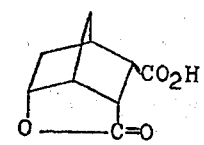 II

Five hundred grams (500 g.) of concentrated sulfuric acid was slowly added with vigorous stirring to a suspension of 164 g. of endo-cis-bicyclo[2.2.1]hept-5-ene-2,3-dicarboxylic anhydride in 500–600 ml. of water. The reaction was exothermic and the temperature rose to about 80°–90° C. during the addition of the sulfuric acid. Two liters of boiling water was added to the reaction solution and immediately filtered. As the filtrate was cooled, colorless platlets of the title product (II) crystallized. On completion of the crystallization, the crystals were collected by filtration and washed with cold water to produce 138 grams of air-dried crystals, m.p. 200° C.

EXAMPLE 2

General Method of Preparation of 5-endo-Hydroxy-N-[amino(lower)alkyl]bicyclo[2.2.1]heptane-2,3-di-endocarboxylic Acid Imides (III).

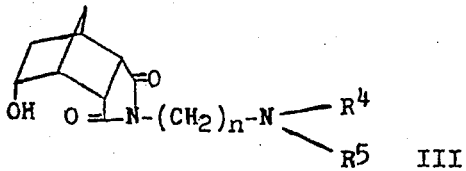

A mixture of 0.1 mole of lactone (II) from example 1 and 50 ml. of acetyl chloride was refluxed on a water bath for 2 hours. The excess acetyl chloride was removed in vacuo and an oily residue (IIa) remained that was washed with n-hexane (or petroleum ether). The oily residue was dissolved in 50 ml. of anhydrous benzene. To this solution was added a solution of 0.12 moles of the appropriate amine, e.g., N,N-dimethylaminopropylamine, and 100 ml. of anhydrous benzene with stirring. The mixture was then refluxed for about 5 hours and concentrated in vacuo. The resultant brown syrupy substance (IIb) was refluxed for 5 hours in 300 ml. of 0.12 mole of potassium hydroxide and 50% water-ethanol. The solvents were removed in vacuo, saturated potassium carbonate solution added and the resultant solution extracted repeatedly using chloroform or 1:1 ethyl acetate-benzene. The collective organic extracts were washed with saturated sodium chloride solution and dried over anhydrous sodium sulfate. After filtration, the solution was concentrated in vacuo and the product was recovered by crystallization, chromatography and/or vacuum distillation wherein in formula III, $n$ is an integer of 2 to 4 inclusive, $R^4$ or $R^5$ is H, (lower)alkyl or when taken together with the nitrogen a radical of the formula

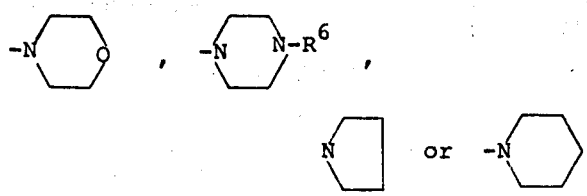

in which $R^6$ is (lower)alkyl.

EXAMPLE 3

General Method of Preparation of 5-endo-substituted-carbamoyloxy-N-[amino(lower)alkyl]bicyclo[2.2.1]-heptane-2,3-di-endo-carboxylic Acid Imides (I).

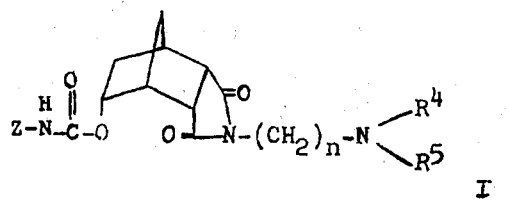

The 5-endo-Hydroxy-N-[amino(lower)alkyl]-bicyclo[2.2.1]heptane-2,3,-di-endo-carboxylic acid imide (III) (0.01 mole) obtained in example 2 is added to 50 ml. of pyridine solution of 0.012 mole of an appropriate isocyanate, e.g., phenyl isocyanate, with stirring. The resultant is refluxed for about 4 hours. The pyridine is removed in vacuo with the aid of added toluene. The resultant oil is dissolved in ethyl acetate, washed with water and brine, dried over anhydrous sodium sulfate, filtered, and the solvent removed to give an oil. Addition of Et$_2$O-Skellysolve B (essentially n-hexane) gives the free amine as a white solid which recrystallizes from an appropriate solvent. The amine is slurried in 20 ml EtOH and HCl gas is bubbled in to give a solution. The addition of Et$_2$O produces a precipitate which is the monohydrochloride salt of the desired product.

EXAMPLE 4

Alternate Method of Preparation of 5-endo-Hydroxy-N-[amino(lower)alkyl]bicyclo[2.2.1]heptane-2,3-di-endo-carboxylic Acid Imides (III).

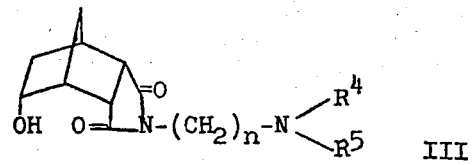

A mixture of 0.1 mole of lactone (IIa) from example 1 above and 30 ml. of PCl$_3$ was refluxed in a water bath for 2 hours. The excess PCl$_3$ was removed in vacuo and washed with n-hexane. The oily residue was dissolved in 50 ml. of chloroform or methylene chloride and a solution of 0.12 mole of an appropriate amine, e.g., N, N-dimethyl-aminopropylamine, dissolved in 100 ml. of anhydrous chloroform or methylene chloride was added with stirring and cooling. Stirring was continued for 2 hours, following which mixture was warmed to room temperature following which the mixture was refluxed for about 15 minutes. The solution was washed with saturated potassium carbonate solution after cooling, separated, and the organic phase washed with saturated sodium chloride solution. The organic solution was dried over anhydrous sodium sulfate, filtered, and concentrated in vacuo. The material subsequently collected was the title product of formula III wherein $n$ is an integer of 2 to 4 inclusive, $R^4$ or $R^5$ is H, (lower)alkyl or when taken together with the nitrogen a radical of the formula

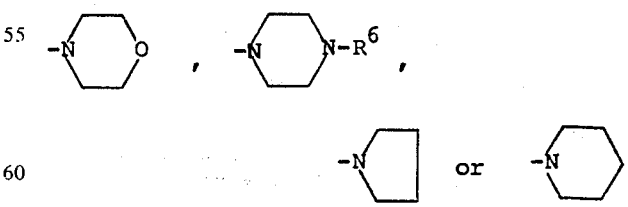

in which $R^6$ is (lower)alkyl.

EXAMPLE 5

Preparation of 5-endo-Hydroxy-N-(3-dimethylaminopropyl)-bicyclo[2.2.1]heptane-2,3-di-endo-carboxylic Acid Imide (IIIa).

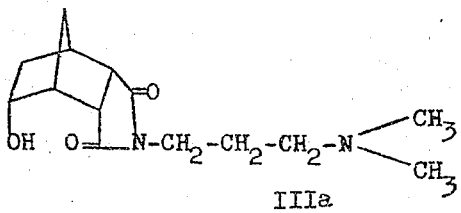

IIIa

Substitution in the procedure of example 2 or 4 of an equimolar quantity of N,N-dimethylaminopropylamine for the "appropriate" amine used therein produced the title product as colorless plates when crystallized from ethanol-n-hexane; m.p. 148° C. (1¾ H₂O) or 154° C. (⅓ H₂O). Yield: 26–37%

Anal. calc'd. for $C_{14}H_{22}O_3N_2 \cdot 1¾H_2O$: C, 56.42; H, 8.79; N, 9.40. Found: C, 56.70; H, 8.76; N, 9.11.

Anal. calc'd. for $C_{14}H_{22}O_3N_2 \cdot ⅓ H_2O$: C, 61.76; H, 8.45; N, 10.29. Found: C, 61.93; H, 8.76; N, 10.40.

EXAMPLE 6

Preparation of (+)-5-endo-N-phenylcarbamoyloxy-(3-dimethylaminopropyl)-bicyclo[2,2,1]heptane-2,3-di-endo-carboxylic acid imide, hydrochloride [Compd. 1, Table I (BL-4507)].

Method A

A mixture of 5-endo-hydroxy-N-(3-dimethylaminopropyl)-bicyclo[2.2.1]heptane-2,3-di-endo-carboxylic acid imide (2.66 g, 0.01 mole) and phenylisocyanate (1.19 g, 0.01 mole) in 30 ml of pyridine was refluxed (110° C) for 4 hours. The pyridine was then removed by evaporation under reduced pressure with the aid of added toluene. The resultant oil was dissolved in EtOAc, washed with water and brine, dried (anhyd. Na₂SO₄) and the solvent removed to give an oil (3.26 g). Addition of Et₂O-Skellysolve B (essentially n-hexane) gave the free amine as a white solid which was recrystallized from EtOAc-Skelly B (2.2 g, mp 133°–135°). The amine was slurried in 20 ml EtOH and HCl gas was bubbled in to give a solution. Addition of Et₂O caused an oil to separate. Decanting, and boiling the oily residue in EtOAc gave a white solid. (2.0 g; 47.79; mp 204°–206°). Recrystallization from MeOH-Et₂O, followed by trituration in boiling EtOAc gave an analytical sample of the anhydrous salt. (mp 205°–208° C.)

Anal. calc'd. for $C_{21}H_{27}N_3O_4 \cdot HCl$: C, 59.76; H, 6.69; N, 9.96. Found: C, 59,74; H, 6.63; N, 9.84.

Method B

A mixture of 5-endo-hydroxy-N-(3-dimethylaminopropyl)-bicyclo[2.2.1]heptane-2,3-di-endo-carboxylic acid imide (2.66 g, 0.01 mole) and phenylisocyanate (4.76 g, 0.04 mole) in 25 ml of methylene chloride (dry) was stirred at 25°C under anhydrous conditions for 18 hours. The methylene chloride was then removed by evaporation under reduced pressure to yield an oil. Trituration with Skelly B-ether yielded a white solid which was recrystallized from hot isopropyl alcohol (3.45 g, mp 134°–135° C, 89%). The hydrochloride salt was prepared as in Method A. (2.7 g; 64.2%; mp 206°–207°C).

EXAMPLE 7

Preparation of (+)-5-endo-N-(o-Chlorophenyl)carbamoyl-oxy-N-(3-dimethylaminopropyl)bicyclo[2.2.1]heptane-2,3-di-endo-carboxylic acid imide, hydrochloride. (Compd. 4, Table I).

Method C

A mixture of 5-endo-hydroxy-N-(3-dimethylpropyl)-bicyclo[2.2.1]heptane-2,3-di-endo-carboxylic acid imide (5.32 g, 0.02 mole) and o-chlorophenylisocyanate (15 ml) in 15 ml of dry pyridine was stirred at 25°C under anhydrous conditions for 18 hours. The reaction mixture was diluted with 100 ml Et₂O, precipitating a white solid, which was then crystallized from 100% EtOH. (6.81 g, 84%, mp 162°–163°C).

Anal. calc'd. for $C_{21}H_{25}N_3O_4Cl$; C, 60.06; H, 6.24; N, 10.01; Cl, 8.44. Found: C, 59.98; H, 6.14; N, 9.83; Cl, 8.40.

EXAMPLE 8

General Method of Preparation of 5-endo-benzoyloxy-N-[amino(lower)alkyl]bicyclo[2.2.1]heptane-2,3-di-endo-carboxylic Acid Imides (L).

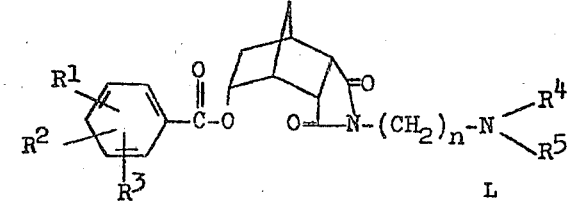

L

The 5-endo-Hydroxy-N-[amino(lower)alkyl]-bicyclo[2.2.1]heptane-2,3-di-endo-carboxylic acid imide (III) (0.01 mole) obtained in example 2 was added to 50 ml. of a 100:1 pyridine-piperidine solution of 0.012 mole of an appropriate benzoyl halide, e.g., benzoyl chloride, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (L).

EXAMPLE 9

Preparation of 5-endo-Benzoyloxy-N-(3-dimethylaminopropyl)bicyclo[2.2.1]heptane-2,3-di-endo-carboxylic Acid Imide (Lb).

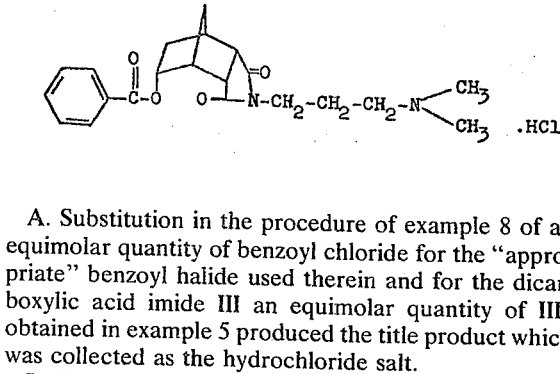

A. Substitution in the procedure of example 8 of an equimolar quantity of benzoyl chloride for the "appropriate" benzoyl halide used therein and for the dicarboxylic acid imide III an equimolar quantity of IIIa obtained in example 5 produced the title product which was collected as the hydrochloride salt.

B. The free base was dissolved in near boiling ethanol (700 ml.) and 90 ml. of ethanol saturated with hydrogen chloride gas was added. The solution was cooled with ice to produce colorless plates of the hydrochloride salt of formula Lb; m.p. 239° C. with decomposition upon recrystallization from methanol-acetone. Yield-90%.

Anal. calc'd. for $C_{21}H_{27}O_4N_2Cl \cdot \frac{1}{3} H_2O$: C, 61.07; H, 6.83; N, 6.95. Found: C, 60,63; H, 6.88; N, 7,33.

EXAMPLE 10

Resolution of (+)-5-endo-Benzoyloxy-N-(3-dimethylaminopropyl)bicyclo[2.2.1]heptane-2,3-di-endocarboxylic Acid Imide Hydrochloride (Lb).

I. Preparation of the (−)-enantiomer.

A. (+)-5-endo-Benzoyloxy-N-(3-dimethyl-aminopropyl)bicyclo[2.2.1]heptane-2,3-di-endo-carboxylic Acid Imide (Lb).

A stirred mixture of the hydrochloride salt of Lb (10 g.) in water (150 ml.) and ether (200 ml.) was neutralized by the addition of sodium carbonate. The aqueous layer was re-extracted with ether (2 × 200 ml.). The combined ethereal extracts were washed with water, followed by water saturated with sodium chloride (3×) and dried (sodium sulfate). Removal of the ether left colorless crystals of the racemic base Lb (9.3 g.), m.p. 106°–107.5°.

B. (+)-10-Camphorsulfonic Acid Salt of (−)-5-endo-benzoyloxy-N-(3-dimethylaminopropyl)-bicyclo[2.2.1]heptane-2,3-di-endo-carboxylic Acid Imide.

A hot solution of (+)-10-camphorsulfonic acid (276.5 g., 1.19 mole) in ethanol (1.1 L) was added to a hot solution of the racemic base Lb (441.1 g., 1.19 mole) in ethanol (3.5.1) containing water (175 ml.). The solution was heated to near boiling and then rapidly cooled to 20°. The colorless crystalline material which formed during 3 hours standing at 20° was collected and washed with cold ethanol (600 ml.) to give 325.3 g. of the title product, m.p. 221°–226°. The salt was recrystallized from acetonitrile to give colorless needles (282.6 g.), m.p. 230°–233°. The ethanolic mother liquor was retained for isolation of the (+)-isomer.

C. (−)-5-endo-Benzoyloxy-N-(3-dimethyl-aminopropyl)bicyclo[2.2.1]heptane-2,3-di-endo-carboxylic Acid Imide.

The camphorsulfonic acid salt from step B (282.6 g.) was partitioned between a stirred mixture of ethyl acetate (3.5.1) and water (3.1) containing sodium carbonate (150 g.). The aqueous layer was reextracted with ethyl acetate (600 ml.). The combined ethyl acetate extracts were washed with water saturated with sodium chloride (3×), and dried (sodium sulfate). Removal of the ethyl acetate left the title product as colorless crystals (173.3 g.): m.p. 131-5-132.5°; $[\alpha]_D^{25}$ −78.53° (c. 4.26, ethanol).

D. (−)-5-endo-Benzoyloxy-N-(3-dimethyl-aminopropyl)bicyclo[2.2.1]heptane-2,3-di-endo-carboxylic Acid Imide Hydrochloride (V).

To a near boiling solution of the (−)-isomer (173.3 g., 0.468 mole) from step C in 95% ethanol (3.5.1) was added 475 ml. of 95% ethanol, 0.988 molar in hydrogen chloride (0.468 mole of HCl). The solution was cooled in ice. The colorless crystals were collected, washed with cold 95% ethanol (600 ml.) and dried to give the title product (182.6 g.): m.p. 207°–209°; $[\alpha]_D^{25}$ −85.56° (c. 1.5, water). The m.p. and rotation were not significantly changed upon further recrystallization from 95% ethanol.

II. Preparation of the (+)-enantiomer.

A. (−)-Tartaric Acid Salt of (+)-5-endo-benzoyloxy-N-(3-dimethylaminopropyl)bicyclo[2.2.1]heptane-2,3-di-endocaarboxylic Acid Imide.

The ethanolic mother liquor from step I B. above was stored at 0° for 90 hours to give additional cyrstalline material (237.2 g.), m.p. 182°–186°. The filtrate was concentrated to give another crop of colorless crystals (119.9 g.), m.p. 168°–177°. Both crops were combined and partitioned between ethyl acetate and aqueous sodium carbonate as described in I C. above to give a mixture of (+)- and (−)- isomers (221.4 g.), m.p. 125°–129°, greatly enriched in the (+)-enantiomer.

(−)-Tartaric acid (89.6 g., 0.596 mole) was added to a hot stirred solution of the (+)-enriched mixture (221.4 g., 0.596 mole) in ethanol (3.6.1) containing water (40 ml.). The stirred mixture was heated to near boiling and then cooled to 25° during 4 hours. The colorless crystalline material was collected, washed with cold 95% ethanol (500 ml.) and dried to give the tartrate salt of the (+)-enantiomer (291.6 g.), m.p. 157°–161° (dec.). Recrystallization from acetonitrile gave 247.2 g. of the purified tartrate salt, m.p. 162°–164° (dec.).

B. (+)-5-endo-Benzoyloxy-N-(3-dimethyl-aminopropyl)bicyclo[2.2.1]heptane-2,3-di-endo-carboxylic Acid Imide.

The tartrate salt from step A (247.2 g.) was decomposed with aqueous sodium carbonate and the liberated (+)-enantiomer extracted into ethyl acetate as described in I.C. Removal of the ethyl acetate left the (+)-isomer (171.6 g.), as colorless crystals: m.p. 131°–133.5°; $[\alpha]_D^{25}$+ 77.74° (c. 1.89, ethanol).

C. (+)-5-endo-Benzoyloxy-N-(3-dimethylaminopropyl)bicyclo[2.2.1]heptane-2,3-di-endo-carboxylic Acid Imide Hydrochloride (VI).

The (+)-enantiomer (171.6 g.) from step B was treated with an equivalent of ethanolic hydrogen chloride as described for the (−)enantiomer in I D. to give colorless crystals of the (+)-enantiomer HCl; (188.2 g.): m.p. 207°–209°; $[\alpha]_D^{25}$ +85.88° (c. 1.36, water).

EXAMPLE 11

(+)-5-Endo-N-phenylcarbamoyloxy-N-(3-dimethylaminopropyl)bicyclo[2.2.1]heptane-2,3-di-endocarboxylic Acid Imide Hydrochloride. [Compd. 2, Table I (BL-4607A)].

(+)-5-Endo-benzoyloxy-N-(3-dimethylaminopropyl)bicyclo[2.2.1]heptane-2,3-di-endo-carboxylic acid imide hydrochloride (3.65 g, 0.0086 mole) was suspended in 18.8 ml. of 1.0N NaOH and heated to reflux with stirring for 45 minutes in an oil bath at 120°–125° C. The solution was then cooled, filtered and evaporated under reduced pressure to yield a white solid. The solid was then triturated with three 80 ml aliquotes of hot EtOAc. The aliquots were combined and evaporated to yield an oil which solidified upon cooling. The solid was then resuspended in 100 ml cyclohexane and 15 ml EtOAc and heated to a reflux. Filtration of the hot solution and cooling to 20° C yielded a crystalline solid (1.53 g; 67% mp 121°–122°C). A mixture of (+)-5-endo-hydroxy-N-(3-dimethylaminopropyl)bicyclo-[2.2.1]heptane-2,3-di-endo-carboxylic acid imide (2.66 g, 0.01 mole) and phenylisocyanate (2.38, 0.02 mole) in 30 ml of dry $CH_2Cl_2$. The method and work-up of the free amine was identical to that in EXAMPLE 1, METHOD B (3.69 g, 95.7%, mp 119°–120°C). The amine was dissolved in 25 ml of EtOAc and HCl gas was bubbled in. The solvent was removed by evaporation under reduced pressure to yield a foam which solidified upon trituration with $Et_2O$. Recrystallization from hot EtOAc: IPA (9:2) gave the pure product. (2.3 g, 54.9%, mp 222°–223°C).

Anal. calc'd. for $C_{21}H_{27}N_3O_4 \cdot HCl$: C, 59.76; H, 6.69; N, 9.96; Cl, 8.40. Found: C, 59.49; H, 6.69; N, 10.01; Cl, 8.30.

$[\alpha]_{589}^{25} = +94.5°$ [C = 0.1366 g; $H_2O$]

EXAMPLE 12

Preparation of (−)-5-endo-N-phenylcarbamoyloxy-N-(3-dimethylaminopropyl)bicyclo[2.2.1]heptane-2,3-di-endo-carboxylic acid imide hydrochloride.

[Compd. 3, Table I(BL-4610A)].

Method - similar to that in Example 11 (3.059 g, 39.5%, mp 223°–223°C).

Anal. calc'd. for $C_{21}H_{27}N_3O_4 \cdot HCl$: C, 59.76; H, 6.69; N, 9.96; Cl, 8.40. Found: C, 60.03; H, 6.73; N, 9.90; Cl, 8.50.

$[\alpha]_{589}^{25} = -95.37°$ [C = 0.080 g, $H_2O$].

The starting material is the (−)-5-Endo-benzoyl-oxy-N-(3-dimethylaminopropyl)-bicyclo[2.2.1]heptane-2,3-di-endo-carboxylicacid imide hydrochloride obtained in example 10.

EXAMPLE 13

Preparation of additional 5-endo-H-substituted carbamoyloxy-N-(3-dimethylaminopropyl)bicyclo[2.2.1-]heptane-2,3-di-endo-carboxylic Acid Imides Substitution in the indicated examples (methods) of the proper equimolar quantities of isocyanate produced the compounds indicated below in Table I.

Table I

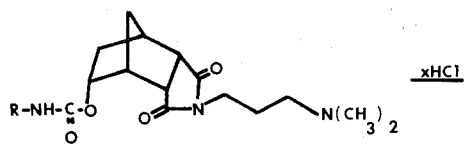

| Compd. No. | R | X | Example (Method) | Yield | M.P. °C | Recrystallization Solvent |
| --- | --- | --- | --- | --- | --- | --- |
| 1 | (±)$C_6H_5$— | 1 | 6A | 47.7 | 204–206 | MeOH-$Et_2O$ |
| 2 | (+)$C_6H_5$— | 1 | 11B | 54.9 | 222–3 | EtOA-IPA |
| 3 | (−)$C_6H_5$— | 1 | 12B | 39.5% | 223–4 | EtOA-IPA |
| 4 | o-ClC$_6$H$_4$— | 0 | 7C | 84% | 162–3° | EtOH |
| 5 | p-OMeC$_6$H$_4$— | 0 | 7C | 72% | 146–7 | IPA |
| 6 | o-OMeC$_6$H$_4$— | 0 | 7C | 70% | 104–5 | IPA |
| 7 | 3,4-diClC$_6$H$_3$— | 0 | 7C | 37% | 152–153 | EtOH |
| 8 | (Cyclohexyl) | 0 | 7C | 28% | 112–113 | Cyclohexane |
| 9 | $H_3C(CH_2)_3$— | 1 | 7C | 72% | 198–9 | IPA-EtOA |
| 10 | 2,4,6-tri$CH_3C_6H_2$— | 0 | 6A | 64.5% | 190 | IPA |
| 11 | p-$CH_3C_6H_4$— | 0 | 7C | 64% | 162–3 | IPA |
| 12 | m-$CF_3C_6H_4$— | 0 | 6B | 51% | 192–3 | IPA |
| 13 | m-$NO_2C_6H_4$— | 0 | 6B | 94% | 151–2 | IPA |
| 14 | p-BrC$_6$H$_4$— | 0 | 6B | 78% | 153–4 | IPA |
| 15 | p-FC$_6$H$_4$— | 0 | 6B | 70% | 160–1 | IPA |
| 16 | p-$CO_2EtC_6H_4$— | 0 | 6B | 92% | 166–7 | IPA |
| 17 | o-$CH_3C_6H_4$— | 0 | 6B | 136–7 | IPA | |
| 18 | 2,5-di$CH_3C_6H_3$— | 0 | 6B | 61.5% | 124 | IPA |
| 19 | 2,6-di$CH_3C_6H_3$— | 0 | 6B | 50% | 148–9 | IPA-$Et_2O$ |
| 20 | 3-pyridyl | 0 | 6B | 29% | 178–9 | IPA |

IPA is isopropyl alcohol.
EtOA is ethyl acetate.
MeOH is methanol.
$Et_2O$ is diethylether.

Analytical Data

| Compd. No. | Calcd C | Calcd H | Calcd N | Found C | Found H | Found N |
| --- | --- | --- | --- | --- | --- | --- |
| 1 | 59.76 | 6.69 | 9.96 | 59.74 | 6.63 | 9.84 |
| 2 | 59.76 | 6.69 | 9.96 | 59.49 | 6.69 | 10.01 |
| 3 | 59.76 | 6.69 | 9.96 | 60.03 | 6.73 | 9.90 |
| 4 | 60.06 | 6.24 | 10.01 | 59.98 | 6.14 | 9.83 |

Analytical Data-continued

| Compd. No. | Calcd C | Calcd H | Calcd N | Found C | Found H | Found N |
| --- | --- | --- | --- | --- | --- | --- |
| 5 | 63.60 | 7.04 | 10.11 | 63.79 | 6.89 | 10.12 |
| 6 | 63.60 | 7.04 | 10.11 | 63.27 | 7.08 | 9.97 |
| 7 | 55.51 | 5.55 | 9.25 | 55.80 | 5.58 | 9.46 |
| 8 | 64.42 | 8.50 | 10.73 | 64.68 | 8.39 | 10.67 |
| 9 | 56.77 | 8.03 | 10.45 | 56.52 | 8.06 | 10.86 |
| 10 | 67.42 | 7.78 | 9.83 | 67.55 | 7.71 | 9.89 |
| 11 | 66.15 | 7.32 | 10.52 | 66.01 | 7.29 | 10.59 |
| 12 | 58.27 | 5.78 | 9.27 | 58.43 | 5.61 | 8.85 |
| 13 | 58.59 | 6.09 | 13.02 | 58.69 | 5.98 | 13.10 |
| 14 | 54.31 | 5.64 | 9.05 | 54.61 | 5.61 | 9.25 |
| 15 | 62.51 | 6.49 | 10.42 | 62.85 | 6.26 | 10.45 |
| 16 | 63.00 | 6.83 | 9.18 | 63.25 | 6.84 | 9.17 |
| 17 | 66.15 | 7.32 | 10.52 | 66.43 | 7.04 | 10.23 |
| 18 | 66.80 | 7.56 | 10.16 | 67.12 | 7.58 | 9.85 |
| 19 | 66.80 | 7.56 | 10.16 | 66.82 | 7.41 | 10.11 |
| 20 | 62.16 | 6.78 | 14.50 | 62.17 | 6.78 | 14.71 |

EXAMPLE 14

General Procedure for the Preparation of the racemic 5-endo-N-carbamoyloxy-N-[amino(lower)alkyl]-bicyclo-[2.2.1]heptane-2,3-di-endo-carboxylic Acid Imides into its (+) and (−) Entantiomers.

1. Treatment of the racemic base with (+)-10-camphorsulfonic acid in ethanol-water gave the diastereoisomeric salt of the (−)-isomer. Decomposition of this salt with aqueous sodium carbonate afforded the (−)-enantiomer which was converted to the hydrochloride with ethanolic hydrogen chloride.

2. The mother liquor from the first step was concentrated to leave a mixture of diastereoisomeric salts. Neutralization of this mixture with aqueous sodium carbonate gave a mixture of the (+)- and (−)-isomers, which was greatly enriched in the (+)-enantiomer. In one small scale experiment, it was possible to obtain substantially pure (+by recrystallization from cyclohexane. In larger scale experiments, it was more expedient to purify the mixture through diastereoisomer formation with (−)-tartaric acid to give the salt of (−)-tartaric acid with the (+)-enantiomer, which is subsequently decomposed to produce the (+)-enantiomer.

EXAMPLE 15

Preparation of 5-endo-Hydroxy-N-(2-dimethylaminoethyl)bicyclo[2.2.1]heptane-2,3-di-endo-carboxylic Acid Imide (IIIb).

Substitution in the procedure of example 4 for the "appropriate" amine used therein of an equimolar quantity of N,N-dimethylethylamine produced the title product which was collected as the hydrochloride using a method comparable to that employed in example 6A. The free base was collected as colorless plates upon recrystallization from ethanol-n-hexane; m.p. 141.5° C. Yield: 50%.

Anal. calc'd. for $C_{13}H_{20}O_3N_2 \cdot 1/3H_2O$: C, 60.46; H, 8.13; N, 10.85. Found: C, 60.71; H, 8.04; N, 10.95.

EXAMPLE 16

Preparation of 5-endo-Hydroxy-N-(2-diethylaminoethyl)bicyclo[2.2.1]heptane-2,3-di-endo-carboxylic Acid Imide Phenolphthalinate (IIIc).

Substitution in the procedure of example 2 for the "appropriate" amine used therein of an equimolar amount of N,N-diethylaminoethylamine produced the title product as yellow oil, b.p. 213°–220° C./5 mm. Hg. Yield: 37%. The product was further characterized as the phenolphthalinate salt, m.p. 137.8°–138.8° C.

Anal. calc'd. for $C_{35}H_{40}O_7N_2 \cdot 1\frac{1}{2} H_2O$: C, 67.04; H, 6.91; N, 4.48. Found: C, 67.38; H, 7.41; N, 4.23.

EXAMPLE 17

Preparation of 5-endo-Hydroxy-N-(3-diethylaminopropyl)bicyclo[2.2.1]heptane-2,3-di-endo-carboxylic Acid Imide Phenolphthalinate (IIIf).

Substitution in the procedure of example 2 for the "appropriate" amine used therein of an equivalent amount of N,N-diethylaminopropylamine produced the title product as a yellow oil, b.p. 228°–230°C./6 mm. Hg. Yield: 34%. The product was further characterized as the phenolphthalinate salt, m.p. 155°–158°C.

Anal. calc'd. for $C_{36}H_{42}O_7N_2 \cdot 1\frac{1}{2} H_2O$: C, 67.39; H, 7.02; N, 4.36. Found: C, 67.77; H, 6.79; N, 4.36.

EXAMPLE 18

Preparation of 5-endo-Hydroxy-N-(3-piperidinopropyl)-bicyclo[2.2.1]heptane-2,3-di-endo-carboxylic Acid Imide (IIIe).

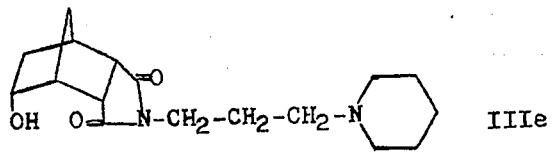

Substitution in the procedure of example 4 for the "appropriate" amine used therein of an equivalent amount of 3-piperidinopropylamine produced the title product as colorless plates upon recrystallization from isopropanol-n-hexane, m.p. 121.5° C. Yield: 50%.

Anal. calc'd. for $C_{17}H_{26}O_3N_2 \cdot \frac{1}{4}H_2O$: C, 65.70; H, 8.53; N, 9.01. Found: C, 66.05; H, 9.03; N, 9.06.

EXAMPLE 19

Preparation of 5-endo-Hydroxy-N-(2-morpholinoethyl)-bicyclo[2.2.1]heptane-2,3-di-endo-carboxylic Acid Imide Hydrochloride (IIIf).

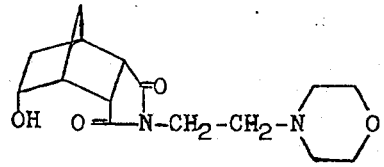

Substitution in the procedure of example 2 or 4 for the "appropriate" amine used therein of an equivalent amount of morpholinoethylamine produced the title compound which was collected as the hydrochloride (using a method comparable to that employed in example 6B). The hydrochloride was collected as colorless plates upon recrystallization from water-ethanol, m.p. 280°–282° C. Yield: 30–34%.

Anal. calc'd. for $C_{15}H_{22}O_4N_2 \cdot HCl$: C, 54.43; H, 7.00; N, 8.46. Found: C, 54.26; H, 7.56; N, 8.50.

EXAMPLE 20

Preparation of 5-endo-Hydroxy-N-(3-morpholinopropyl)-bicyclo[2.2.1]heptane-2,3-di-endo-carboxylic Acid Imide (IIIg).

Substitution in the procedure of example 2 for the "appropriate" amine used therein of an equivalent amount of morpholinopropylamine produced the title product as a yellow oil, b.p. 260°–270° C./4 mm. Hg.; yield 50%. The product was further characterized as the methiodide salt; m.p. 233° C.

Anal. calc'd. for $C_{16}H_{24}O_4N_2 \cdot CH_3I$: N, 6.2 Found: N, 6.28

EXAMPLE 21

Preparation of 5-endo-N-(p-nitrophenyl)carbamoyloxy-N-(3-morpholinopropyl)bicyclo[2.2.1-]heptane-2,3-di-endo-carboxylic acid Imide (Ig).

Substitution in the procedure of example 3 for the "appropriate" isocyanate used therein of an equivalent amount of 4-chlorophenylisocyanate for the dicarboxylic acid imide III used therein an equimolar quantity of IIIg produces the title product.

EXAMPLE 22

Preparation of 5-endo-N-(p-chlorophenyl)carbamoyloxy-N-(3-morpholinopropyl)bicyclo[2.2.1-]heptane-2,3-di-endo-carboxylic acid Imide Hydrochloride (Ih).

Substitution in the procedure of example 3 for the "appropriate" isocyanate used therein of an equivalent amount of 4-chlorophenylisocyanate for the dicarboxylic acid imide III used therein an equimolar quantity of IIIg produces the title product which is collected as the hydrochloride (using a method comparable to that employed in example 6).

EXAMPLE 23

Preparation of 5-endo-N-phenylcarbamoyloxy-N-(2-dimethylaminoethyl)bicyclo[2.2.1]heptane-2,3-di-endo-carboxylic Acid Imide (Ij).

Substitution in the procedure of example 3 for the "appropriate" isocyanate used therein of an equimolar quantity of phenylisocyanate and for the dicarboxylic acid imide an equimolar quantity of IIIb obtained in example 15, produces the title compound.

EXAMPLE 24

Preparation of 5-endo-N-(p-nitrophenyl)carbamoyloxy-N-(3-piperidinopropyl)bicyclo[2.2.1]heptane-2,3-di-endo-carboxylic Acid Imide (Ik).

Substitution in the procedure of example 3 for the "appropriate" isocyanate used therein of an equimolar quantity of p-nitrophenylisocyanate and for the dicarboxylic acid imide III used therein of IIIe produces the title compound.

EXAMPLE 25

Preparation of 5-endo-N-phenylcarbamoyloxy-N-(2-dimethyl-aminoethyl)bicyclo[2.2.1]heptane-2,3-di-endo-carboxylic Acid Imide.

Substitution in the procedure of example 3 for the "appropriate" isocyanate used therein of an equimolar amount of phenylisocyanate and for the dicarboxylic acid amide III used therein an equimolar quantity of IIIb produces the title compound.

EXAMPLE 26

Preparation of 5-endo-N-phenylcarbamoyloxy-N-(3-methylaminopropyl)bicyclo[2.2.1]heptane-2,3-di-endo-carboxylic Acid Imide Hydrochloride (Ij).

A. 5-endo-N-phenylcarbamoyloxy-N-[3-(2,2,2-trichloroethoxy-carbonyl)-3-methylamino-propyl]bicyclo[2.2.1]heptane-2,3-di-endo-carboxylic Acid Imide.

Under anhydrous conditions there is added 22 mmoles of trichloroethyl chloroformate to a mixture of 10 mmoles of compound Ib and 2.0 g. (14.5 mmoles) potassium carbonate in 50 ml. benzene. The reaction mixture is refluxed for 18 hours. After cooling, ethyl acetate is added and the solution is filtered from the insolubles. The filtrate is washed with water, 5% $K_2CO_3$, water, 5% HCl, water and brine. After drying ($Na_2SO_4$) and filtration the solvents are evaporated. In this manner, there is obtained a crude product which when recrystallized from ethyl acetate-skelly B (essentially n-hexane) affords title product.

B. 5-endo-N-phenylcarbamoyloxy-N-(3-methylaminopropyl)bicyclo[2.2.1]heptane-2,3-di-endo-carboxylic Acid Imide Hydrochloride.

Zinc dust (11.0 grams) is added to a solution of 5.56 g. (10.5 mmoles) of the compound prepared in A above in 120 ml. of 90% acetic acid. The resulting reaction mixture is stirred at room temperature for four hours. The mixture is filtered and the filtrate evaporated to dryness. The residue is made basic by the addition of sodium bicarbonate and again is evaporated to dryness. Benzene (500 ml.) and $Na_2SO_4$ is added to the residue. The mixture is filtered; the filtrate is evaporated and the residue is dissolved in methanol. Some ether is added, and the hydrochloride salt is prepared with anhydrous hydrogen chloride gas. The precipitated salt is collected and after several recrystallizations from methanol-ether, there is obtained the title compound (Ij).

EXAMPLE 27

Preparation of 5-endo-N-phenylcarbamoyloxy-N-(3-aminopropyl)bicyclo[2.2.1]heptane-2,3-di-endo-carboxylic acid imide (Ik).

A. endo-5-Hydroxy-bicyclo[2.2.1]heptane-endo-2[N-(2-cyanoethyl)]carboxamide-endo-3-carboxylic acid γ-lactone (XX).

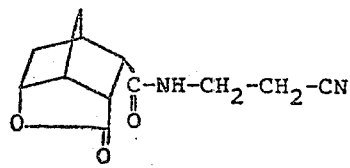

XX

A mixture of lactone-acid II (18.2 g; 0.1 mole), 150 ml. $SOCl_2$ and 250 ml $CH_2Cl_2$ containing 4 drops DMF (dimethylformamide) was refluxed (60°C) for 3 hours. After evaporating to dryness, benzene was added and removed under reduced pressure. After dissolving the acid chloride in 350 $CH_2Cl_2$, there was added dropwise with vigorous stirring a solution of 3-aminopropionitrile (15.3 g; 0.21 mole) in 150 ml $CH_2Cl_2$. The resulting reaction mixture was refluxed for 2 hours. After cooling and filtering the insoluble materials, the filtrate was evaporated to dryness. The residue, so obtained, was slurried with a small amount of $CH_3CN$ to which ether was carefully added. In this way, the crystalline product was obtained in 85.5% yield with mp 129°–135°C. A sample of recrystallization from $CH_3CN$ gave analytically pure material, mp 145°–147°C.

Anal. calc'd. for $C_{12}H_{14}N_2O_3$: C, 61,52; H, 6.02; N, 11.96. Found: C, 61.54; H, 6.28; N, 11.96

B. 5-endo-N-phenylcarbamoyloxy-N-(2-cyanethyl)-bicyclo[2.2.1]heptane-endo-2,3-dicarboxylic acid imide (XI).

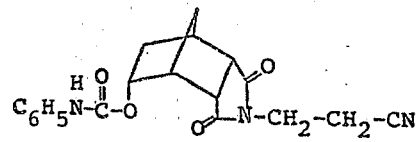

XI

To a solution of lactone-amide XX (16 g; 0.068 mole) in 200 ml pyridine is added slowly the phenylisocyanate (0.102 mole). The resulting reaction mixture is heated to 110°C for 4 hours. After evaporation to dryness, 5% $K_2CO_3$ is added and the mixture is extracted with ethyl acetate. The extracts are washed with brine, dried over $Na_2SO_4$, filtered and evaporated to dryness. Addition of ethanol and petroleum ether to the residue affords the product.

C. 5-endo-N-phenylcarbamoyloxy-N-(3-aminopropyl)bicyclo[2.2.1]heptane-endo-2,3-dicarboxylic acid imide hydrochloride (Ik).

A mixture of imide-nitrile XI (1.0 g; 2.96 mmole), 200 mg 10% Pd on carbon, 5 ml 5N HCl, and 95 ml ethanol are shaken under hydrogen at room temperature for 19 hours. After this time, water is added to the reaction mixture until all the solids dissolve. The catalyst is removed and the filtrate is evaporated to dryness, thereby affording the product.

We claim:

1. A compound having the formula

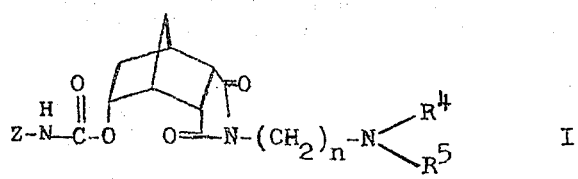

I in which Z is a radical of the formula

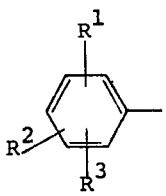

wherein $R^1$, $R^2$ or $R^3$ is H, Cl, Br, F, (lower)alkyl, nitro, OH or (lower)alkoxy, $n$ is an integer of 2 to 4 inclusive and $R^4$ or $R^5$ is H, (lower)alkyl or when taken together with the nitrogen a radical of the formula

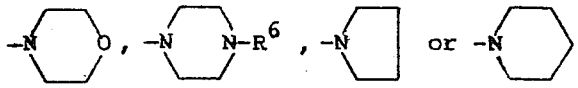

in which $R^6$ is (lower)alkyl; or a pharmaceutically acceptable acid addition salt thereof.

2. A compound of claim 1 having the formula

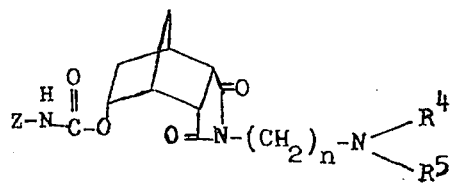            I in which Z is a radical of the formula

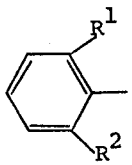

wherein $R^1$ and $R^2$ are alike or different and each is H, Cl, Br, F, (lower)alkyl, nitro, OH or (lower)alkoxy, $n$ is an integer of 2 to 4 inclusive and $R^4$ or $R^5$ is H, (lower)alkyl or when taken together with the nitrogen a radical of the formula

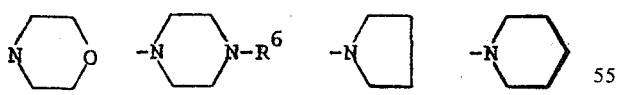

in which $R^6$ is (lower)alkyl; or a pharmaceutically acceptable acid addition salt thereof.

3. A compound of claim 2 wherein $R^1$ and $R^2$ are alike or different and each is H, F, Cl, nitro or (lower)alkyl, $R^4$ or $R^5$ is H, (lower)alkyl or when taken together with the nitrogen a radical of the formula

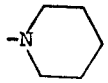  

4. A compound of claim 2 wherein $R^1$ and $R^2$ are (lower)alkyl, $R^4$ and $R^5$ are (lower)alkyl or when taken together with the nitrogen a radical of the formula

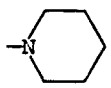  or  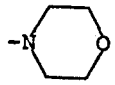

5. A compound of claim 2 wherein $R^1$ is hydrogen, $R^2$ is chloro, $n$ is an integer of 3 and $R^4$ and $R^5$ are methyl; or the hydrochloride salt thereof.

6. (±)-5-Endo-N-phenylcarbamoyloxy-N-(3-dimethylaminopropyl)bicyclo[2.2.1]heptane-2,3-di-endo-carboxylic acid imide; or the hydrochloride salt thereof.

7. The compound of claim 2 wherein $R^1$ and $R^2$ are hydrogen, $n$ is an integer of 2 and $R^4$ and $R^5$ are methyl; or the hydrochloride salt thereof.

8. The compound of claim 1 in which Z is

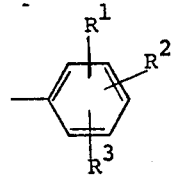

wherein $R^1$ and $R^3$ are hydrogen, $R^2$ is p-methyl, $n$ is an integer of 3 and $R^4$ and $R^5$ taken together with the nitrogen is a radical of the formula

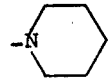

or the hydrochloride salt thereof.

9. The compound of claim 1 in which Z is

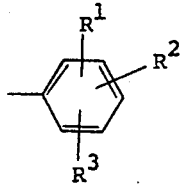

wherein $R^1$ and $R^3$ are hydrogen, $R^2$ is p-chloro, $n$ is an integer of 3 and $R^4$ and $R^5$ taken together with the nitrogen is a radical of the formula

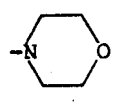

of the hydrochloride salt thereof.

10. The compound of claim 1 in which Z is

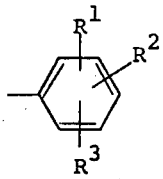

wherein $R^1$ and $R^3$ are hydrogen, $R^2$ is p-nitro, *n* is an integer of 3 and $R^4$ and $R^5$ when taken together with the nitrogen is a radical of the formula

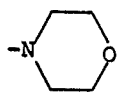

of the hydrochloride salt thereof.

11. The compound of claim 1 in which Z is

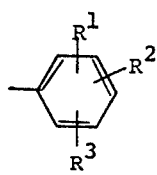

wherein $R^1$ and $R^3$ are hydrogen, $R^2$ is methyl, hydrogen or p-nitro, *n* is an integer of 3 and $R^4$ and $R^5$ are each (lower)alkyl; or the hydrochloride salt thereof.

12. The compound of claim 1 in which Z is

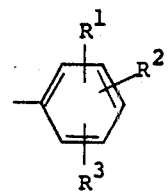

wherein $R^1$ and $R^3$ are hydrogen, $R^2$ is p-nitro, n is an integer of 3 and $R^4$ and $R^5$ are methyl; or the hydrochloride salt thereof.

13. The essentially pure levorotatory isomers of the compounds of claim 1.

14. The essentially pure levorotatory isomers of the compounds of claim 2.

15. The essentially pure levorotatory isomer of the compound of claim 6; or the hydrochloride salt thereof.

16. The essentially pure dextrorotatory isomer of the compound of claim 6; or the hydrochloride salt thereof.

\* \* \* \* \*